United States Patent
Bruchmann et al.

(10) Patent No.: US 7,257,445 B2
(45) Date of Patent: Aug. 14, 2007

(54) WELDED CONNECTOR ATTACHMENT

(75) Inventors: Richard A. Bruchmann, Andover, MN (US); Thomas Ceballos, Spring Lake Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 316 days.

(21) Appl. No.: 10/974,286

(22) Filed: Oct. 27, 2004

(65) Prior Publication Data

US 2006/0089680 A1 Apr. 27, 2006

(51) Int. Cl.
*A61N 1/372* (2006.01)

(52) U.S. Cl. .......................................... 607/36; 607/37

(58) Field of Classification Search ............. 607/36–38
See application file for complete search history.

(56) References Cited

U.S. PATENT DOCUMENTS

| 3,683,932 | A | * | 8/1972 | Cole ........................... 607/37 |
| 4,254,775 | A | * | 3/1981 | Langer ......................... 607/5 |
| 6,574,508 | B2 | | 6/2003 | Zaouali et al. |
| 2003/0040780 | A1 | | 2/2003 | Haeg et al. |
| 2003/0045911 | A1 | * | 3/2003 | Bruchmann et al. .......... 607/36 |
| 2004/0116976 | A1 | | 6/2004 | Spadgenske |
| 2004/0122481 | A1 | | 6/2004 | Tidemand et al. |

\* cited by examiner

*Primary Examiner*—Carl Layno
*Assistant Examiner*—Jessica L. Reidel
(74) *Attorney, Agent, or Firm*—Daniel G. Chapik; Girma Wolde-Michael (57) ABSTRACT

Methods and apparatus for an implantable medical device having a connector module that is welded to a housing. The apparatus comprises an implantable medical device that includes a housing and a connector module. The connector module includes an embedded fastener bracket with one or more weld tabs that are welded to the housing.

34 Claims, 7 Drawing Sheets

WELDED CONNECTOR ATTACHMENT

TECHNICAL FIELD

The present invention relates generally to implantable medical devices and, more particularly, the present invention relates to attachment of a connector module to a housing by welding.

BACKGROUND

Implantable medical devices (IMDs) detect and administer therapy for a variety of conditions. IMDs may include implantable pulse generator (IPG), cardiac pacemakers, pacemaker-cardioverter-defibrillators, nerve, muscle and neurological stimulators, cardiomyostimulators, implantable drug dispensers, implantable cardiac signal monitors and recorders and the like. IMDs typically include a housing that encloses a variety of internal components and isolates them from the implanted environment. IMDs may include integrated circuits, charging capacitors, batteries, and other components that are enclosed in hermetically sealed housings. Within the human body, for example, the housing must be sealed to prevent ingress of fluids which can cause the device to short circuit or corrode internal components, rendering the IMD inoperable.

Figure 1:
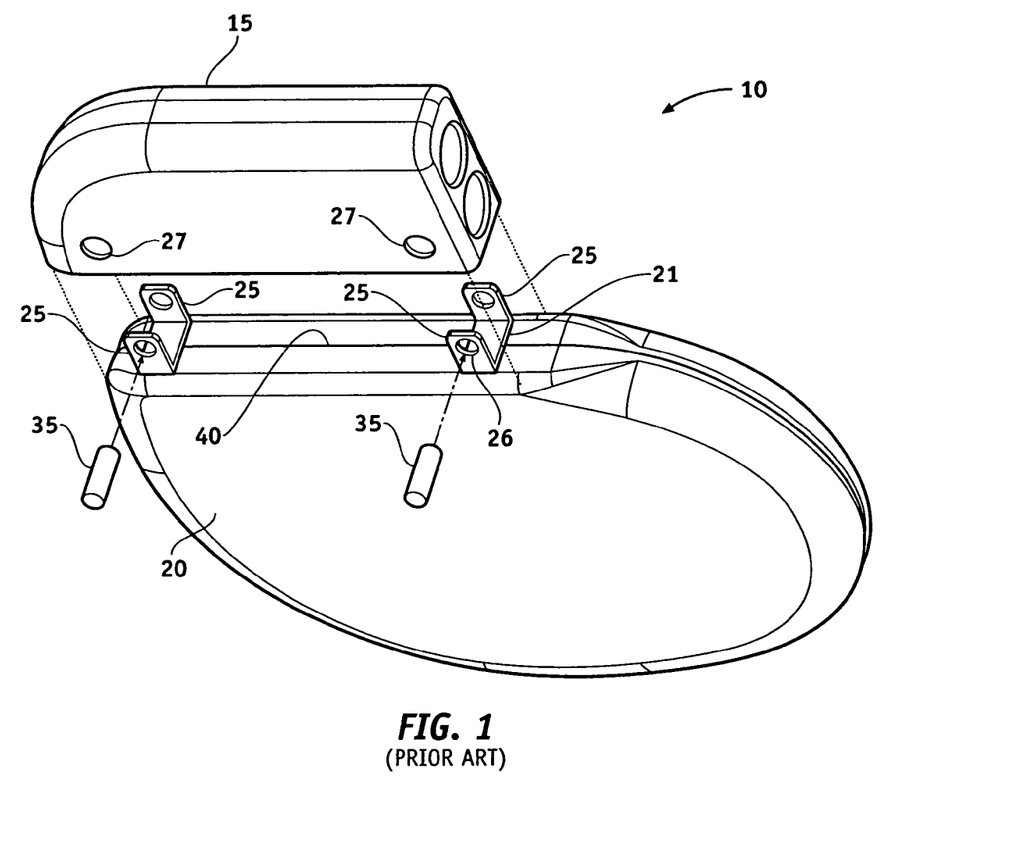
FIG. 1 is a cross-sectional view of implantable medical device showing a prior art attachment scheme of a connector module to a housing.

In many systems, components within the IMD housing are coupled electrically to components that are outside of the housing. One way of connecting electrical components outside of the housing is through a connector module that is securely attached to the outside of the housing. FIG. 1 is a cross-sectional view of an IMD 10 showing a prior art attachment scheme of a connector module 15 to the outside of a housing 20. A plurality of attachment brackets 25 are positioned on the mating surface of the housing 20. These brackets 25 are commonly U or L-shaped, with one leg or portion of the bracket attached to the housing 20 by bonding or welding 21. The other leg of the bracket 25 extends away from the housing 20 and includes an attachment hole 26. The bottom of the connector module 15 includes openings that are sized to accept the attachment bracket legs when assembled. The connector module 15 also includes attachment holes 27 that align with the attachment holes 26 in the attachment bracket legs when assembled. During assembly, the connector module 15 is placed over the attachment brackets 25 and pins 35 are inserted through the mating holes of each component to hold the connector module 15 to the housing 20. In addition to the pins 30, medical adhesive 40 may be placed between the connector module 15 and housing 20.

Manufacturability is a significant concern in the design of implantable medical devices. The above-described manufacturing method has many steps and components to attach the connector module to the housing. In addition, there are many close tolerances that have to be met for the components to fit together properly. Efforts to simplify or reduce the complexity, cost, and time of the manufacturing process can directly impact the cost of the implantable medical device for patients. Accordingly, it is desirable to provide a more simple and cost-effective manufacturing process for use in the attachment of the connector module to the housing. Furthermore, other desirable features and characteristics of the present invention will become apparent from the subsequent detailed description and the appended claims, taken in conjunction with the accompanying drawings and the foregoing technical field and background.

BRIEF SUMMARY

An apparatus is provided for an implantable medical device that simplifies and/or reduces the complexity, cost, and time of attaching a connector module to a housing over the prior art. The above and other aspects of the invention may be carried out in one form by an implantable medical device that includes a housing, a connector module, and a fastener bracket with one or more weld tabs. The fastener bracket is embedded in the connector module, becoming part of the connector module. The weld tabs are attached to the housing by welding.

In other embodiments of the invention, the housing contains electrical components and the connector module includes one or more receptacles that are in electrical contact with the electrical components. The housing may also be hermetically sealed. The housing may also include one or more recesses that are sized to accept the one or more weld tabs.

An implantable medical device system is disclosed that includes an implantable medical device connected to one or more leads. The implantable medical device includes a housing that contains at least one electrical component and a connector module. The connector module includes one or more receptacles electrically coupled to the at least one electrical component. A fastener bracket with one or more weld tabs is embedded in the connector module and the weld tabs are connected to the housing by welding. The one or more leads include one or more electrodes and are electrically coupled to the one or more receptacles in the connector module.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

The invention may be described herein in terms of components and various processing steps. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Figure 2:
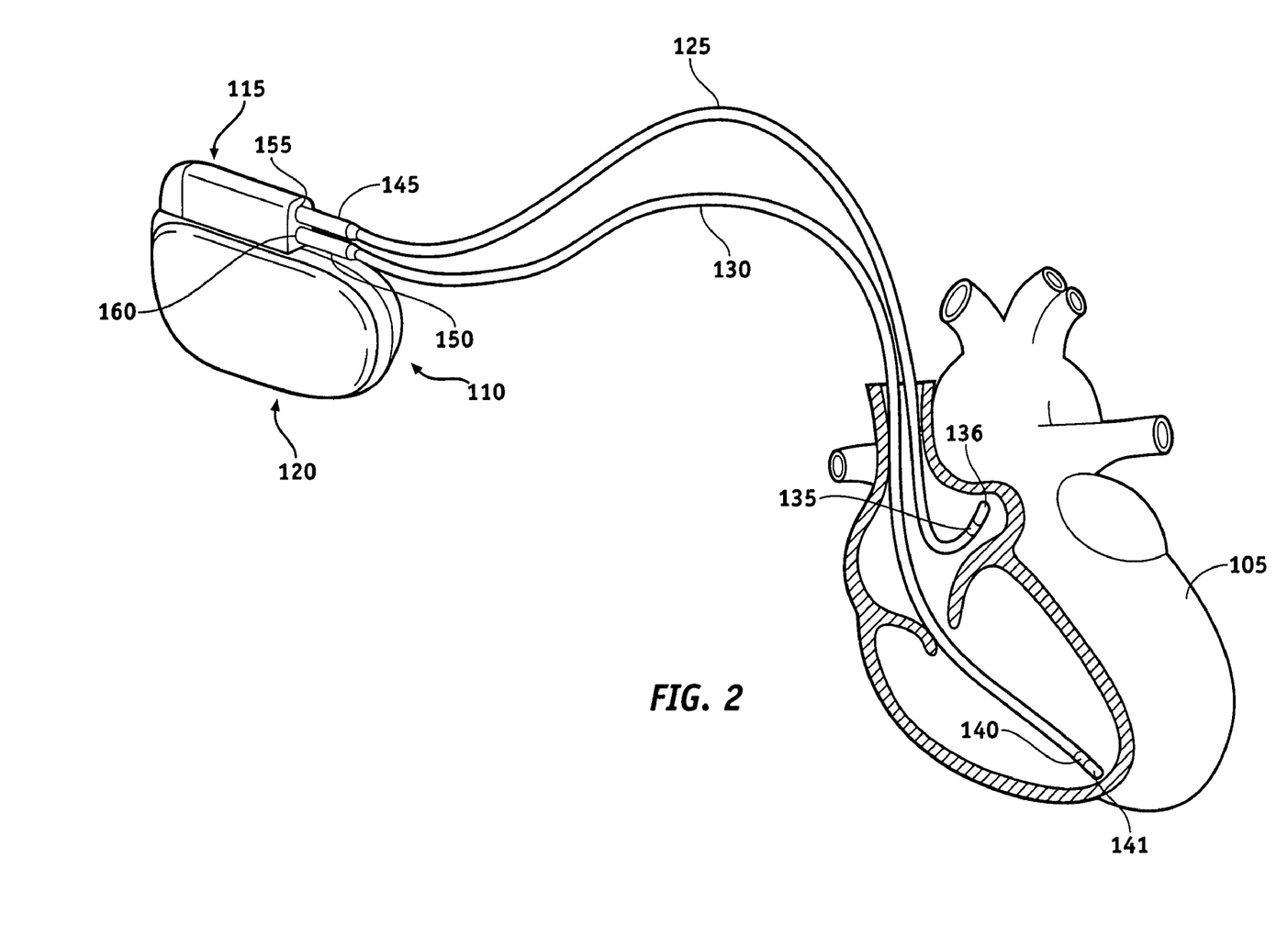
FIG. 2 shows an implantable medical device system in which the present invention may be practiced.

FIG. 2 depicts connector module 115 and hermetically sealed enclosure 120 of implantable medical device (IMD) or dual chamber pacemaker IPG 110 of the present invention as they relate to patient's heart 105. Atrial and ventricular pacing leads 125 and 130 extend from connector header module 115 to the right atrium and ventricle, respectively. Atrial electrodes 135 and 136 disposed at the distal end of the atrial pacing lead 125 are located in the right atrium. Ventricular electrodes 140 and 141 at the distal end of ventricular pacing lead 130 are located in the right ventricle.

Connector module 115 may take any of the forms described herein for establishing electrical and mechanical connections of proximal connector end assemblies 145 and 150 of the atrial and ventricular pacing leads 125 and 130 to electrical or electronic circuitry disposed within hermetically sealed enclosure 110. Connector module 115 therefore preferably incorporates connector blocks (not shown) within the module housing that are aligned with elongated lead connector end receptacles 155 and 160, and that are adapted to receive lead connector end assemblies 145 and 150. Any other lead, fixation mechanism, and/or electrode configuration known in the art may be used with the current invention, and those shown are exemplary only. Feedthroughs and feedthrough pins connected to the connector blocks and extending through the hermetically sealed enclosure 120 are also not shown in FIG. 2. Connector module 115 may be molded of a rigid thermoplastic material such polyurethane, polysulfone or any other such suitable medical grade thermoplastic material.

Figure 3:
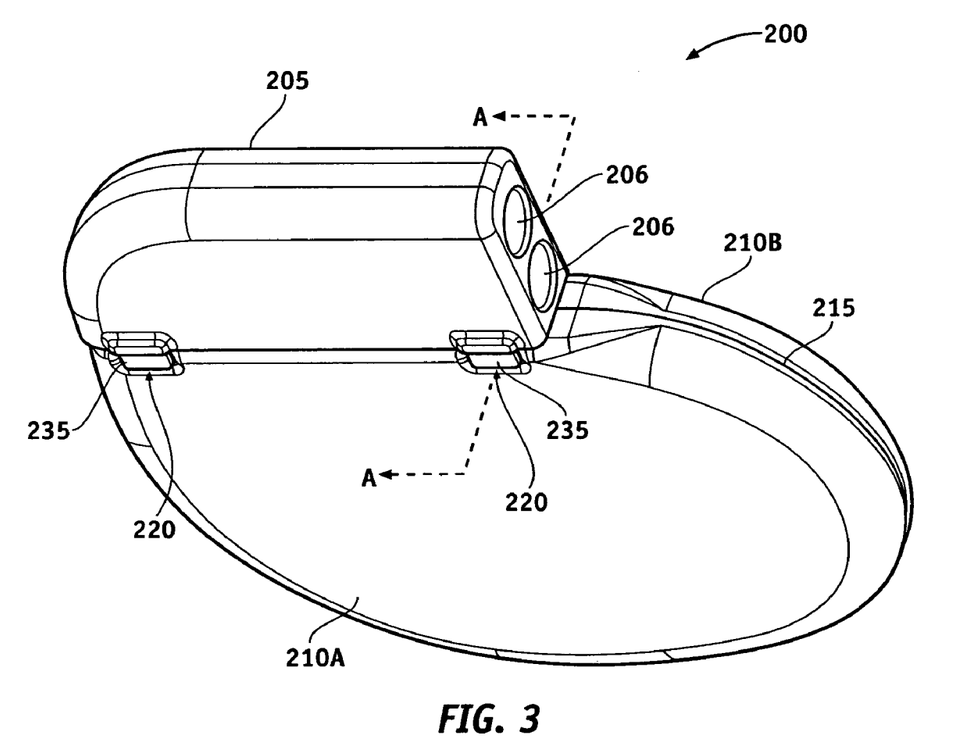
FIG. 3 is a perspective exterior view of an implantable medical device.

While atrial and ventricular pacing leads are shown in FIG. 2, other leads are contemplated at other locations in the body that may monitor and/or deliver therapy. For example, other embodiments may include neuro leads for neuro therapy systems; drug leads drug delivery systems; stimulation leads for stimulation therapy systems; sensor leads for monitoring activity; or other compatible monitor and/or treatment delivery leads for other systems. FIG. 3 illustrates an exemplary implantable medical device (IMD) 200 in which the present invention may be practiced. It will be understood that the present invention may be practiced with any other type of implantable device, including, but not limited to, pacemakers, cardioverter/defibrillators, and drug delivery devices. The IMD 200 includes a connector module 205 connected to a hermetically-sealed housing comprising first and second shields 210a and 210b connected together by a welded connection 220 to define a seam 215. The seam 215 is welded following placement of internal components, such as one or more electrical components, within the shields 210a, 210b to hermetically seal the IMD 200. Together, the shields 210a, 210b define an enclosure for internal components that may include an internal battery, a charging capacitor, electronic circuitry, and other suitable components. The one or more electrical components within the housing may be coupled electrically to components that are outside of the housing. For example, one or more medical electrical leads, such as those shown in FIG.2, may be coupled to receptacles 206 of the connector module 205. The electrical connections between the receptacles 206 and the electrical components inside the housing are generally made by conductors extending between the connector module 205 and the internal electrical components. To protect internal electrical components while permitting electrical connections with external components, the housing includes one or more feedthroughs (not shown) that preserves the environmental integrity of the device.

Figure 4:
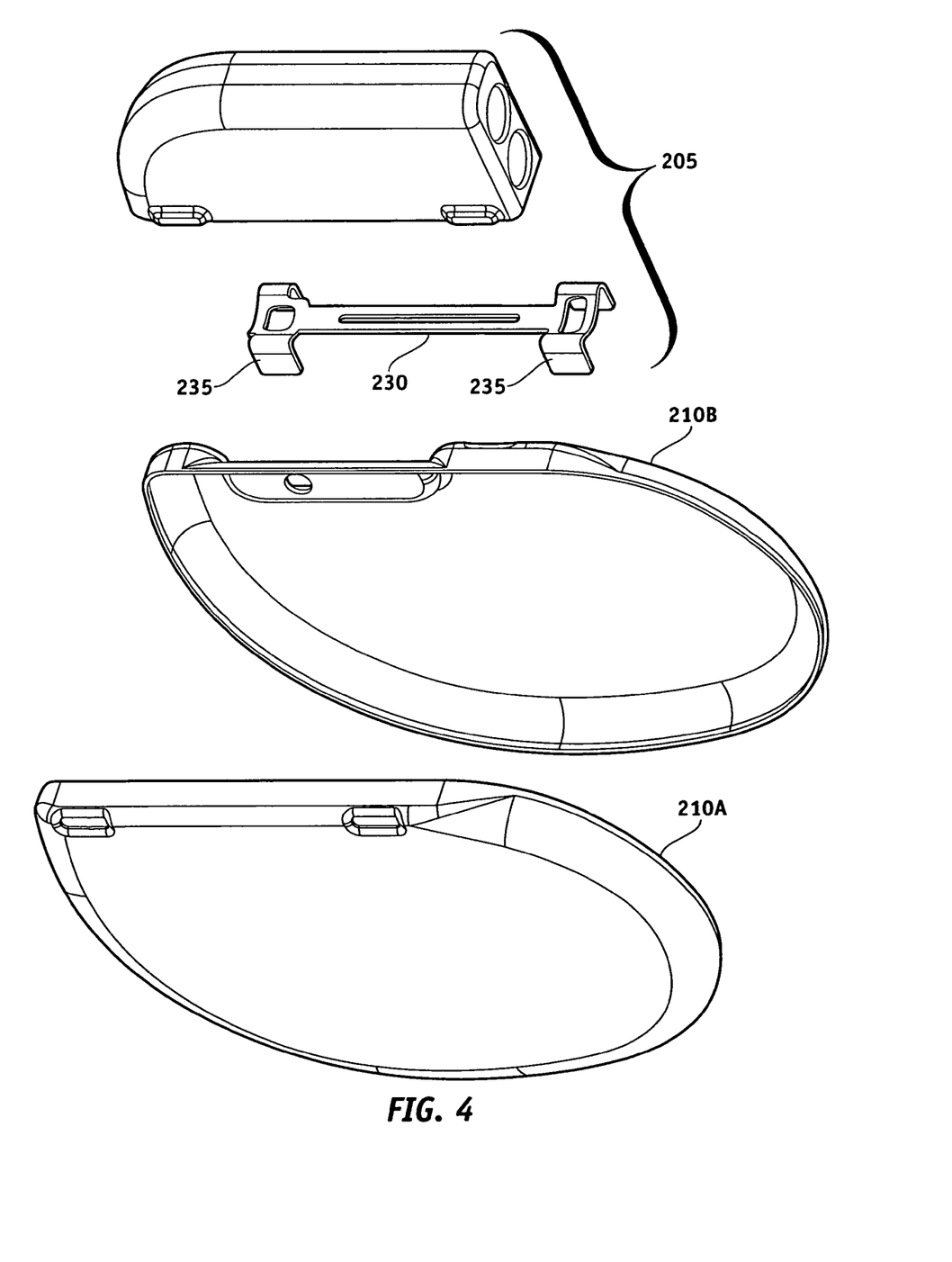
FIG. 4 is an exploded perspective view of the device of FIG. 3.

FIG. 4 is an exploded view of FIG. 3 showing the some of the components of the IMD 200 including the connector module 205 and first and second shields 210a, 21Ob. Many of the components, such as electrical components and feedthroughs, have been omitted for clarity and are known to those skilled in the art. The connector module 205 includes a body with an embedded fastener bracket 230. The body is made of a biocompatible composite material, such as polyurethane, polysulfone or any other such suitable medical grade thermoplastic material. The fastener bracket 230 is made of a medical grade metal, such as titanium, nickel-cobalt, gold, stainless steel, any other such suitable medical grade material that is weldable. In one embodiment, the fastener bracket 230 is embedded into the body by known means, such as insert-molding or over molding. The fastener bracket 230 includes one or more weld tabs 235 that extend outside the body for attachment to shield 210a and/or shield 210b by welded connection 220. The shields 210a, 210b are made of a biocompatible material that the weld tabs 235 may be welded to, such as titanium, nickel-cobalt, gold, stainless steel, any other such suitable medical grade material that is weldable.

As can be seen in the figures, the present invention provides an IMD that simplifies and/or reduces the complexity, cost, and time of the manufacturing over the prior art. In addition, a welded connection provides a more robust attachment of the connector module to the housing than pin attachment. The welded connection provides welds that are in shear, making them stronger than the welds that are in tension. The fastener bracket may be inexpensively stamped with the required weld tabs, with one stamped fastener bracket replacing up to twelve prior art components, such as fasteners and/or pins, of the previous IMD designs (see FIG. 1). Imbedding the fastener bracket into the connector module also reduces piece part count and mold complexity. Fixture cost of the shield assembly is reduced because of fastener/pin elimination. Fixture cost of connector module attachment to the housing is reduced because of automation, which could not be performed with the previous designs. Welding provides higher attachment strength (shear) than the previous fastener/pin design (peel). There are no piece part inventories, such as fasteners or pins, required at final assembly of the connector module to the housing.

Figure 5:
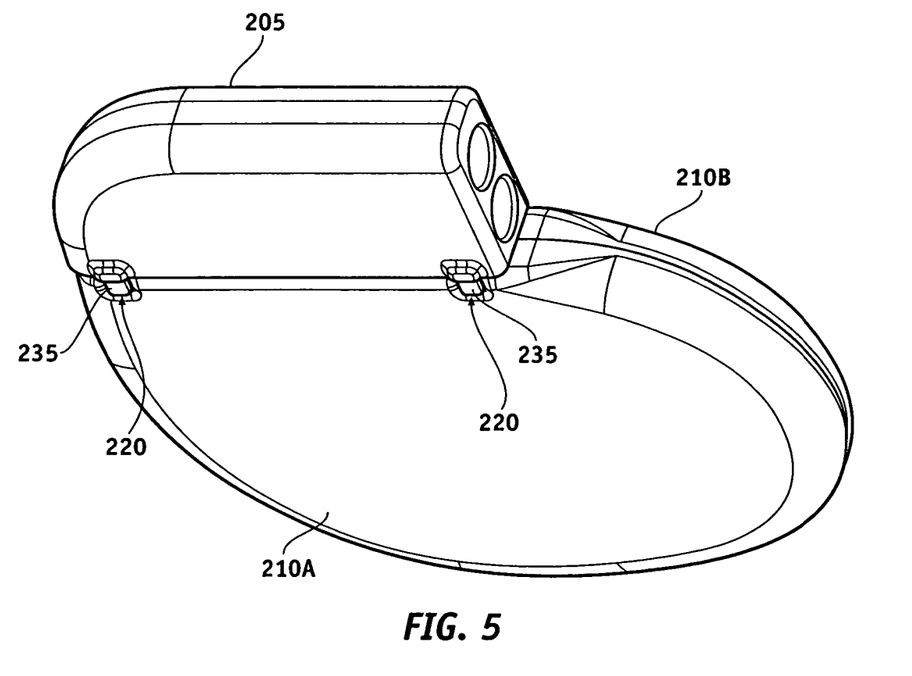
FIG. 5 is a perspective exterior view showing another embodiment of an implantable medical device.

The number, position and size of the weld tabs may vary depending on the design. In the embodiment shown in FIG. 4, there are four weld tabs positioned on the fastener bracket 230, two on each side, for attachment to the housing. In other embodiments, there may be more or fewer weld tabs 235 on each side of the fastener bracket 230. For example, in FIG. 3 there are two medium sized weld tabs 235 on each side positioned near the ends of the connector module 205. FIG. 5 shows two smaller weld tabs 235 positioned near the ends of the connector module 205. In the embodiment shown in FIG. 6, there is one attachment tab 235 on one side extending along the length of the connector module 205.

FIGS. 7-10 are cross-sectional views taken along A-A of FIG. 3 showing various configurations for attaching the connector module to the housing. In the embodiment shown in FIG. 7, each of the housing shields 210a and 210b includes a recess 240 that is sized and positioned for mating with a weld tab 235. The connector module 205 is positioned for assembly by placing the weld tabs 235 into the recesses 240. The weld tabs 235 are then welded to the housing shields 210a and 210b by known means, such as laser welding. It is envisioned that the positioning of the components and welding may be automated to reduce cost and time. In other embodiments, the housing may include no recesses, with the connector module welding to the side of the housing or there may only be recesses 240 in only one shield of the housing (see also FIG. 9).

Figure 7:
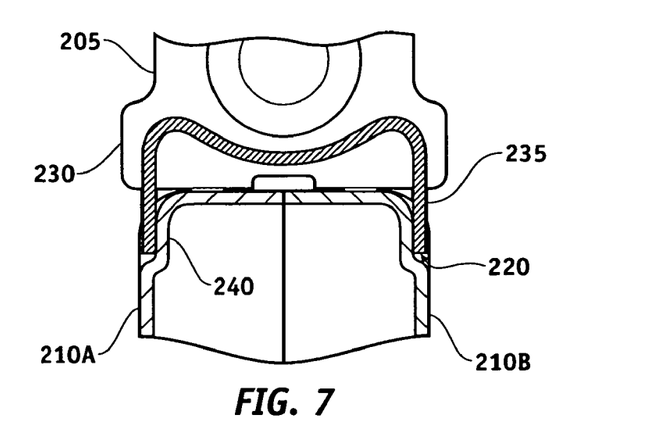
FIGS. 7-10 are cross-sectional views along line A-A of FIG. 3 showing different configurations for attaching the connector module to the housing.
Figure 8:
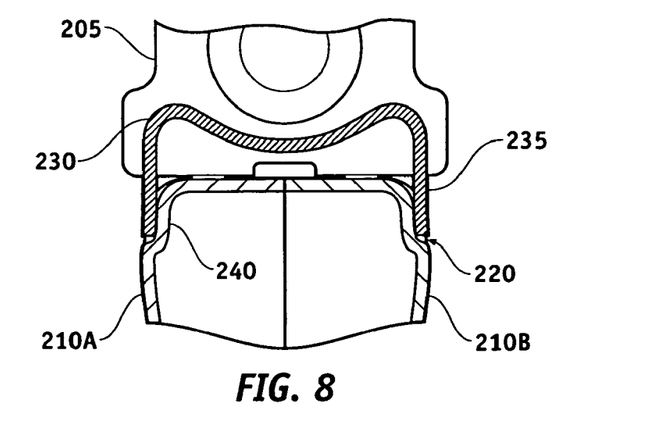

FIG. 8 is similar to FIG. 7 except that the recesses 240 in the housing shields 210a and 210b are tapered or ramped, such that the weld tabs 235 are bent outward with an interference fit when they contact the tapered recess 240. The angle of each ramp may be varied. The connector module 205 is positioned for assembly by sliding the weld tabs 235 into the tapered recesses 240 until they stop. The weld tabs 235 are then welded 220 to the housing shields 210a and 210b. This may be useful in fixturing of the components and may compensate for housing thicknesses.

Figure 9:
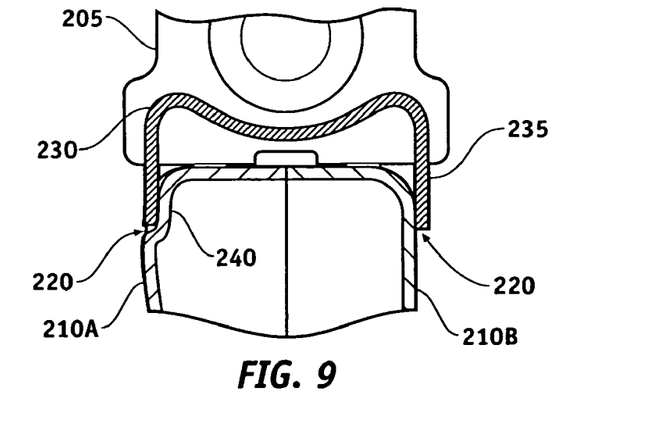

FIG. 9 is similar to FIG. 8 except that there the recesses 240 are only in one shield, in this case shield 210a. Some of the weld tabs 235 are positioned in the recesses 240 and some of the weld tabs 235 of the connector module 205 extend to the side of the housing, as shown on the right side of the figure. Once in place, the weld tabs 235 are welded to the housing.

Figure 10:
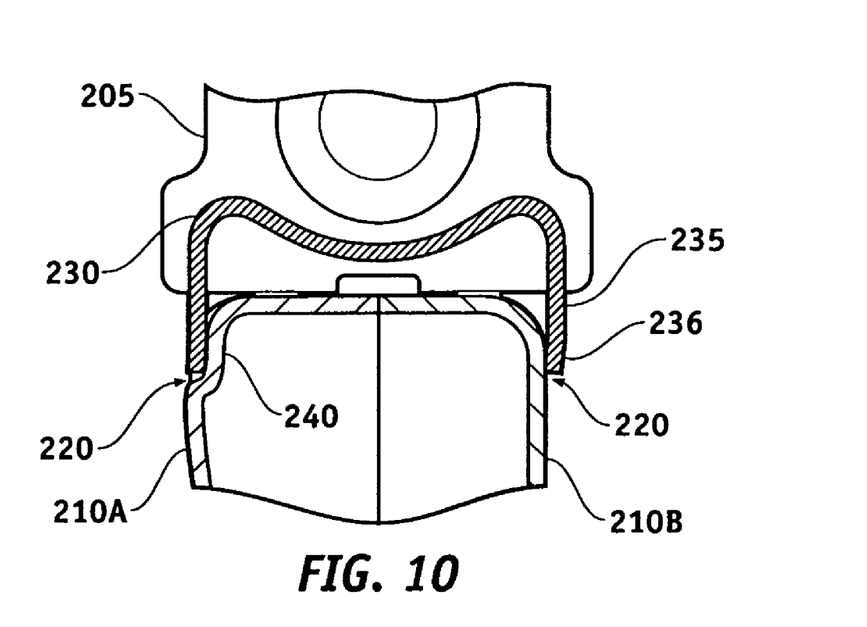

FIG. 10 is similar to FIG. 9, except that the weld tab 235 attached to the side of the housing shield 210b has a bend in feature 236. The bend in feature 236 may be on only selected tabs or all weld tabs 235. The bend in feature 236 may be used with straight recesses 240 (such as shown in FIG. 7) or tapered or ramped recesses 240 (such as shown in FIG. 8). The bend in feature 236 may be useful to create an interference fit with the housing 210. Once in place, the weld tabs 235 are welded to the housing shield 210b. This may be useful in fixturing of the components and may compensate for housing thicknesses.

Figure 6:
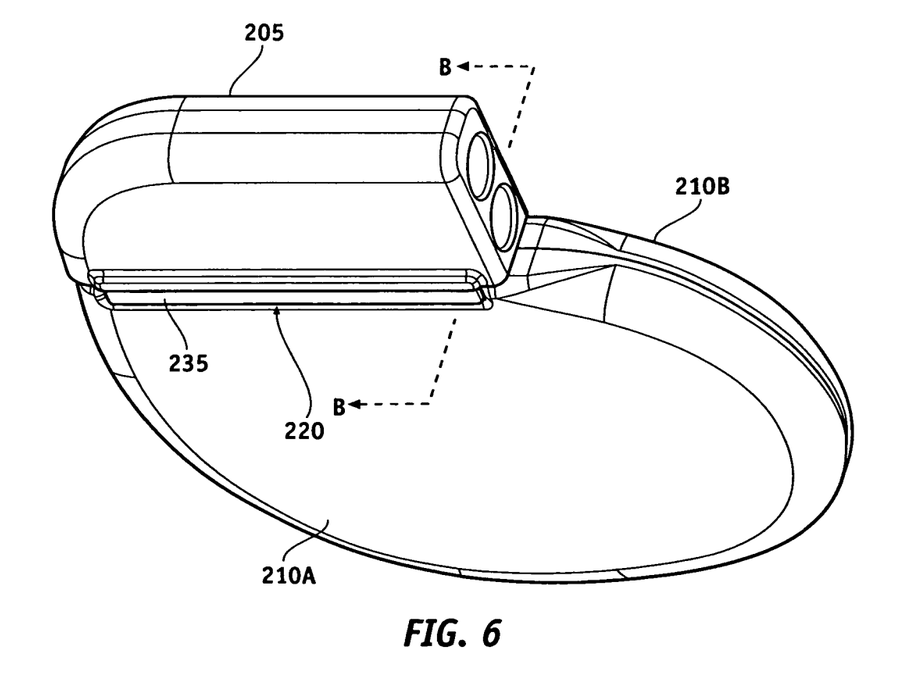
FIG. 6 is a perspective exterior view showing still another embodiment of an implantable medical device.
Figure 11:
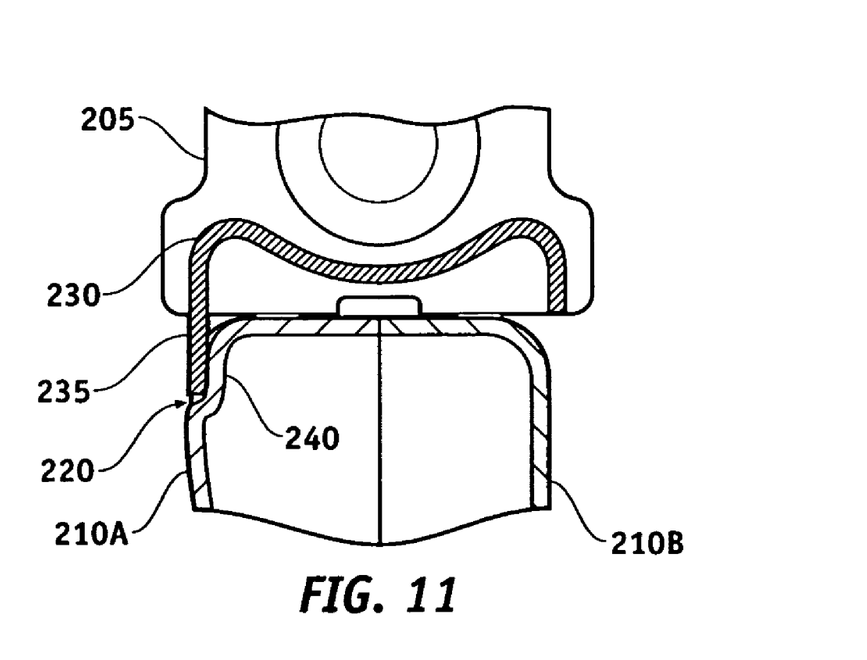
FIG. 11 is a cross-sectional view along line B-B of FIG. 6 showing a configuration for attaching the connector module to only one side of the housing.

FIG. 11 is a cross-sectional view taken along B-B of FIG. 6. This embodiment illustrates the attachment of the connector module 205 to only one shield of the housing, either the first shield 210a or the second shield 210b. In the embodiment shown in FIG. 11, the housing includes one or more recesses 240 in the first shield 210a that are sized for the one or more weld tabs 235. The connector module 205 is positioned for assembly by placing the one or more weld tabs 235 into the recesses 240. The weld tabs 235 are then welded to the first shield 210a. The use of the recesses and the weld tabs may be useful in aligning and fixturing of the components. This embodiment is not dependent on the thickness of the housing shields 210a and 210b. In other embodiments, the one or more weld tabs 235 may be welded to the side of the housing shields 210a and 210b, without any recesses, if it is determined that recesses in the housing are undesirable or not needed.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

The invention claimed is:

1. An implantable medical device, comprising:
   a closed housing having an exterior top surface and opposing exterior side surfaces;
   a connector module mounted to the exterior top surface of the housing;
   a fastener bracket embedded in the connector module and becoming part of the connector module, the fastener bracket having one or more weld tabs extending outside the connector module and overlaying an exterior side surface of the housing;
   a weld connection of the one or more fastener bracket weld tabs to the exterior side surface of the housing serving to affix the connector module to the and wherein the housing further includes one or more recesses sized to accept the one or more weld tabs.

2. The device of claim 1, wherein the connector module is made of a biocompatible medical grade thermoplastic material.

3. The device of claim 2, wherein the material is polyurethane.

4. The device of claim 1, wherein the fastener bracket is made of a biocompatible, weldable material.

5. The device of claim 4, wherein the material is selected from the group consisting of titanium, nickel-cobalt, gold, stainless steel and any other such suitable medical grade material that is weldable.

6. The device of claim 1, wherein the housing is made of a biocompatible, weldable material.

7. The device of claim 6, wherein the material is selected from the group consisting of titanium, nickel-cobalt, gold, stainless steel and any other such suitable medical grade material that is weldable.

8. The device of claim 1, wherein the housing further includes first and second shields.

9. The device of claim 8, wherein the one or more weld tabs are connected to only one of the first shield or second shield.

10. The device of claim 8, wherein the one or more weld tabs is one full length attachment tab connected to the first shield or second shield.

11. The device of claim 8, wherein an equal number of weld tabs are connected to each of the first and second shields.

12. The device of claim 1, further comprising;
at least one electrical component inside the housing; and
one or more receptacles in the connector module, wherein the one or more receptacles are electrically coupled to the at least one electrical component.

13. The device of claim 1, wherein the one or more recesses are tapered.

14. The device of claim 1, wherein one or more of the weld tabs include a bend in feature.

15. An implantable medical device system, comprising:
an implantable medical device comprising:
a closed housing having an exterior top surface and opposing exterior side surfaces and that contains at least one electrical component;
a connector module mounted to the exterior top surface of the housing and having one or more receptacles electrically coupled to the at least one electrical component;
a fastener bracket with one or more weld tabs, the fastener bracket being embedded in the connector module so as to become part of the connector module and the one or more weld tabs being welded to an exterior side surface of the housing;
one or more leads electrically coupled to the one or more and wherein the housing further includes one or more recesses sized to accept the one or more weld tabs.

16. The system of claim 15, wherein the one or more leads includes a ventricular lead.

17. The system of claim 15, wherein the one or more leads includes an atrial/superior vena cava lead.

18. The system of claim 15, wherein the one or more leads includes a neuro lead.

19. The system of claim 15, wherein the one or more leads includes one or more electrodes.

20. The system of claim 15, wherein the one or more leads includes one or more sensors.

21. The system of claim 15, wherein the one or more leads are compatible with one or more treatment systems.

22. The system of claim 15, wherein the one or more leads are compatible with one or more drug delivery systems.

23. The system of claim 15, wherein the one or more leads are compatible with one or more neuro therapy systems.

24. The system of claim 15, wherein the one or more leads are compatible with one or more monitoring systems.

25. A method of manufacturing an implantable medical device, comprising:
encasing at least one electrical component inside a closed housing having opposing exterior side and further including one or more recesses sized to accept one or more weld tabs of a connector module; and
welding the one or more weld tabs of the connector module to an exterior side surface of the housing.

26. The method of claim 25, wherein the one or more weld tabs are part of a fastener bracket that is imbedded in the connector module.

27. The method of claim 25, wherein the connector module is made of a biocompatible medical grade thermoplastic material.

28. The method of claim 27, wherein the material is polyurethane.

29. The method of claim 25, wherein the fastener bracket is made of a biocompatible, weldable material.

30. The method of claim 29, wherein the material is selected from the group consisting of titanium, nickel-cobalt, gold, stainless steel and any other such suitable medical grade material that is weldable.

31. The method of claim 25, wherein the housing is made of a biocompatible, weldable material.

32. The method of claim 31, wherein the material is selected from the group consisting of titanium, nickel-cobalt, gold, stainless steel and any other such suitable medical grade material that is weldable.

33. The method of claim 25, further comprising electrically coupling the at least one electrical component to one or more receptacles in the connector module.

34. The method of claim 33, further comprising electrically coupling one or more leads to the one or more receptacles in the connector module.

* * * * *

UNITED STATES PATENT AND TRADEMARK OFFICE

Certificate

Patent No. 7,257,445 B2             Patented: August 14, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: patent is: Richard A. Bruchmann, Andover, MN (US); Thomas Ceballos, Spring Lake Park, MN (US); James Strom, Arden Hill, MN (US); and John E. Nicholson, Blaine, MN (US).

Signed and Sealed this Fifth Day of August 2008.

CARL H. LAYNO
*Supervisory Patent Examiner*
Art Unit 3766